United States Patent
Nammoku et al.

(10) Patent No.: US 9,857,219 B2
(45) Date of Patent: Jan. 2, 2018

(54) NUCLEIC ACID ANALYSIS DEVICE AND DIAGNOSIS METHOD

(71) Applicant: Hitachi High-Technologies Corporation, Minato-ku, Tokyo (JP)

(72) Inventors: Manami Nammoku, Tokyo (JP); Kohshi Maeda, Tokyo (JP); Takehiko Hosoiri, Tokyo (JP); Yasunori Shoji, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/913,809

(22) PCT Filed: Jul. 3, 2014

(86) PCT No.: PCT/JP2014/067774
§ 371 (c)(1),
(2) Date: Feb. 23, 2016

(87) PCT Pub. No.: WO2015/029595
PCT Pub. Date: Mar. 5, 2016

(65) Prior Publication Data
US 2016/0245690 A1 Aug. 25, 2016

(30) Foreign Application Priority Data
Aug. 27, 2013 (JP) .................. 2013-175965

(51) Int. Cl.
*G01J 1/44* (2006.01)
*G01N 21/51* (2006.01)
(Continued)

(52) U.S. Cl.
CPC .................. *G01J 1/44* (2013.01); *G01N 1/30* (2013.01); *G01N 1/38* (2013.01); *G01N 21/51* (2013.01);
(Continued)

(58) Field of Classification Search
CPC ........ G01J 1/44; G01J 2001/444; G01N 1/30; G01N 1/38
See application file for complete search history.

(56) References Cited

U.S. PATENT DOCUMENTS 4,506,375 A * 3/1985 Manson .................... G01T 7/00
250/252.1
6,303,916 B1 * 10/2001 Gladnick ........... H05B 41/3922
250/205
(Continued)

FOREIGN PATENT DOCUMENTS

JP 2-95243 A 4/1990
JP 2590688 Y2 2/1999
(Continued)

OTHER PUBLICATIONS

Japanese Office Action issued in counterpart Japanese Application No. 2015-534065 dated Aug. 30, 2016 (five pages).
(Continued)

*Primary Examiner* — Marcus Taningco
(74) *Attorney, Agent, or Firm* — Crowell & Moring LLP

(57) ABSTRACT

A nucleic acid analysis device is provided that is capable of quickly detecting device abnormalities, and the like. This device is provided with a temperature control block (1) for holding a tube (10) that includes a sample, a photometer (6), and a device diagnosis unit. The photometer (6) is provided with an LED (11) for irradiating light toward the temperature control block (1) in a state in which the tube (10) is held and a fluorescence detector (20) for receiving light emitted by the sample in response to the irradiation of light from the LED (11). The device diagnosis unit causes the LED (11) to irradiate light toward the temperature control block (1) in a state in which the tube (10) is not held, causes the fluorescence detector (20) to detect the resulting scattered light, and
(Continued)

diagnoses the photometer (6) on the basis of the intensity of the scattered light.

9 Claims, 12 Drawing Sheets

(51) Int. Cl.
*G01N 21/64* (2006.01)
*G01N 1/30* (2006.01)
*G01N 1/38* (2006.01)

(52) U.S. Cl.
CPC ...... *G01N 21/645* (2013.01); *G01J 2001/444* (2013.01)

(56) References Cited

U.S. PATENT DOCUMENTS

2009/0311672 A1* 12/2009 Nunn ................... C12Q 1/6848
435/6.11
2012/0194805 A1* 8/2012 Ness ....................... G01N 21/05
356/213
2013/0324816 A1* 12/2013 Bechtel .............. A61B 5/14551
600/331
2014/0170734 A1 6/2014 Shoji et al.

FOREIGN PATENT DOCUMENTS

| JP | 2003-334521 A | 11/2003 |
| --- | --- | --- |
| JP | 2004-37192 A | 2/2004 |
| JP | 2004-251802 A | 9/2004 |
| JP | 4525427 B2 | 8/2010 |
| JP | 2011-185728 A | 9/2011 |
| JP | 2012-37355 A | 2/2012 |
| JP | 2013-21988 A | 2/2013 |

OTHER PUBLICATIONS

International Search Report (PCT/ISA/210) issued in PCT Application No. PCT/JP2014/067774 dated Sep. 22, 2014 with English translation (three pages).
Japanese-language Written Opinion (PCT/ISA/237) issued in PCT Application No. PCT/JP2014/067774 dated Sep. 22, 2014 (three pages).

\* cited by examiner

1: TEMPERATURE ADJUSTING BLOCK  10: TUBE
6: PHOTOMETER                   11: LED
                                20: FLUORESCENCE DETECTOR

NUCLEIC ACID ANALYSIS DEVICE AND DIAGNOSIS METHOD

TECHNICAL FIELD

The present invention relates to a nucleic acid analysis device and a diagnosis method for the same, and relates to, for example, a nucleic acid analysis device for analyzing a biological sample by amplifying nucleic acid included in the biological sample, and a diagnosis method for the same.

BACKGROUND ART

For example, PTL 1 has disclosed a test method for an analysis disk and an analysis device, which is intended for testing an analysis device by irradiating an analysis disk with light and detecting reflection light and transmission light therefrom. In this method, on the basis of the results of detecting the transmission light in a state that the analysis disk is not attached and the results of detecting the reflection light and the transmission light in a state that the analysis disk is attached, the presence or absence of the defect in the analysis disk and the analysis device is determined.

PTL 2 has disclosed the fluorescence detector including the LED for excitation, which irradiates a detection target with excitation light; the light reception unit that receives the fluorescence emitted from the detection target; and a mechanism that monitors the excitation light and feeds back to the LED for excitation so that the excitation light has constant intensity. PTL 3 has disclosed the spectroscopic analysis apparatus that spectrally disperses the measurement light and measures the amount of light for each wavelength with the photodiode array, which employs a method where the degree of deterioration in the photodiode array is determined. In this method, the dark current and the temperature of the photodiode array are measured and then, the value of the dark current is compared with the allowable current value corrected in accordance with the temperature, based on which the degree of deterioration is determined.

CITATION LIST

Patent Literature

PTL 1: Publication of U.S. Pat. No. 4,525,427
PTL 2: JP-A-2012-37355
PTL 3: JP-A-2004-37192

SUMMARY OF INVENTION

Technical Problem

The analysis of nucleic acid included in biological samples such as blood, plasma, and tissue fragments has been employed in various fields of not just academic studies but also industries including diagnosis, selective breeding of agricultural products, and food testing. The most popular method for analyzing the nucleic acid is the technique called PCR (Polymerase Chain Reaction), in which the base sequence of the nucleic acid in a region to be analyzed is amplified specifically. In PCR, the reaction solution including nucleic acid and a reagent for amplifying the nucleic acid is heated to approximately 95° C. so that the nucleic acid is thermally denatured. After that, the temperature is reduced to approximately 60° C. so that the annealing and the extension reaction of the nucleic acid are advanced. This cycle is repeated by 30 to 40 times. For detecting the amplification of the nucleic acid along with the advancing reaction, a method is often employed in which: the fluorescence label whose fluoresce intensity changes depending on the amount of generated PCR is mixed in the reaction solution; the mixed reaction solution is irradiated with the excitation light; and then, the fluorescence intensity emitted from the fluorescence label is measured.

In general, the reaction solution in which the reagent or the like is mixed with the nucleic acid to be analyzed is analyzed as soon as the preparation is done. This is in order to prevent the enzyme included in the reagent or the nucleic acid to be analyzed from deteriorating over time. Another reason is to minimize the possibility of the non-specific annealing or extension reaction different from the desired nucleic acid sequence after the mixing of the nucleic acid and the reagent.

An analysis executer activates the nucleic acid analysis device after preparing the reaction solution in which the reagent or the like is mixed in the nucleic acid to be analyzed. Some nucleic acid analysis devices cannot start the analysis soon after the activation, in which case the device may be activated before the preparation. The nucleic acid analysis device carries out the analysis by delivering the light to the sample and receives the light (fluorescence) emitted from the sample. On this occasion, the accurate analysis may be failed if the important components of the nucleic acid analysis device, i.e., the LED (Light Emitting Diode) or the semiconductor laser as the light source, or the detector such as a PD (Photodiode) or a CCD (Charge Coupled Device), are in trouble or have deteriorated in performance. In the field of medicals, in particular, the wrong analysis result can lead to a crucial problem. For this reason, it has been required that the trouble or performance deterioration of such important components of the nucleic acid analysis device is detected early and a warning is issued.

It is the most desirable that such a trouble or performance deterioration is known before the reagent or the like is mixed into the nucleic acid. However, even though it is not known beforehand, the reaction solution can be saved in a refrigerator so as not to be wasted, if just after the preparation. If it is turned out that the component is in trouble or has deteriorated in performance after the PCR reaction is started, usually, the analysis from the PCR reaction is no longer effective. In view of this, the trouble or performance deterioration in the nucleic acid analysis device is desirably detected while the analysis is awaited after the activation of the device (i.e., before the PCR reaction is started). On this occasion, it is required that the trouble or the performance deterioration is detected in a shorter time in order to shorten the standby time for the analysis and improve the throughput. Moreover, for the quick repair, it is desired to detect the broken component.

For solving the problem, for example, the techniques as disclosed in PTL 1 to PTL 3 may be used. With the technique according to PTL 1, the abnormality of the measurement system can be detected before the sample is actually measured. In the technique according to PTL 1, however, the abnormality in the measurement system can be determined but it is difficult to specify the component that has caused the abnormality (for example, whether the component is the light source, detector, or any other component). In addition, the technique according to PTL 1 requires the process of attaching and detaching the analysis disk, so that it may take time to detect the abnormality in the measurement system. That is to say, the throughput of the device may be deteriorated.

In the case of using the technique according to PTL 2, the PD that monitors the excitation light from the LED for excitation is provided, although it is not for the purpose of detecting the trouble of the component. By using this, the trouble of the light source or the like can be detected. However, although the trouble of the light source and the like can be detected, it is difficult to detect the trouble of the detector or the like.

Similarly, in the case of using the technique according to PTL 3, the trouble of the detector or the like can be detected but it is difficult to detect the trouble of the light source or the like. Moreover, according to the technique of PTL 3, the trouble of the detector or the like is detected by the dark current that is extremely weak at, for example, the pA level; therefore, it is necessary to mount an advanced current value monitoring function. The initial value of the dark current of the detector varies largely depending on the element, and the influence from the temperature is also large. Therefore, it is not easy to construct the algorithm for determining the trouble, etc.

The present invention has been made in view of the above, and an object thereof is to provide a nucleic acid analysis device and a diagnosis method for the same, which can quickly detect the abnormality of the device or the like.

The aforementioned object and another object of the present invention and the novel characteristics thereof will be made apparent from the description of the specification and the attached drawings.

Solution to Problem

The summary of typical embodiments among the inventions disclosed herein will be described below.

A nucleic acid analysis device according to this embodiment includes a holding member that holds a reaction container containing a sample, a photometer, and a device diagnosis unit. The photometer includes a light source that delivers light toward the holding member in a state of holding the reaction container, and a first detector that receives light emitted from the sample in accordance with the delivery of the light from the light source. The device diagnosis unit performs processes in the embodiment: a first process of causing the light source to deliver light toward the holding member in a state of not holding the reaction container; a second process of causing the first detector to detect scattering light generated in accordance with the first process; and a third process of diagnosing the photometer on the basis of intensity of the scattering light detected by the first detector.

Advantageous Effects of Invention

An effect of the typical embodiments among the inventions disclosed herein is, briefly speaking, the quick detection of the abnormality of the nucleic acid analysis device.

DESCRIPTION OF EMBODIMENTS

In the embodiments below, the description will be divided into a plurality of sections or embodiments if necessary. These are not irrelevant to each other unless stated explicitly, and one is related to the modifications, the details, the supplementary explanation, or the like of part or all of the other. In the embodiments below, the number of components (pieces, numerals, amount, range, etc.) is not limited to the particular number unless explicitly stated or specifically being limited to the particular number in principle, and may be more than or less than the described number.

It is needless to say that, in the embodiments below, the structure elements (including the steps) are not necessarily essential unless explicitly stated or clearly considered necessary in principle. Similarly, in the embodiments below, the shape, the positional relation, and the like of the structure elements include the shape and the like that are substantially the same or similar to those unless explicitly stated or clearly considered inappropriate in principle. This similarly applies to the numeral and the range.

Detailed description is hereinafter made of the embodiments of the present invention with reference to the drawings. Throughout the drawings for describing the embodiment, the same member is generally denoted by the same sign and the overlapping description is omitted.

First Embodiment

<<Structure of Main Part of Nucleic Acid Analysis Device>>

Figure 1:
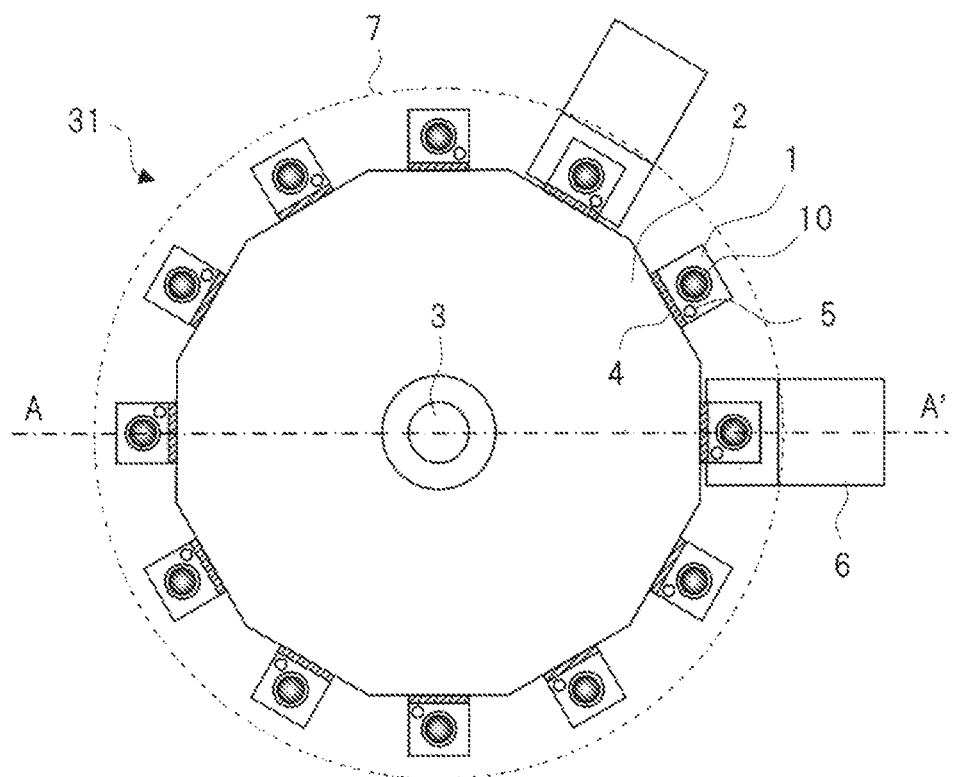
FIG. 1 is a top view illustrating a structure example of a main part of a nucleic acid analysis device according to a first embodiment of the present invention.
Figure 2:
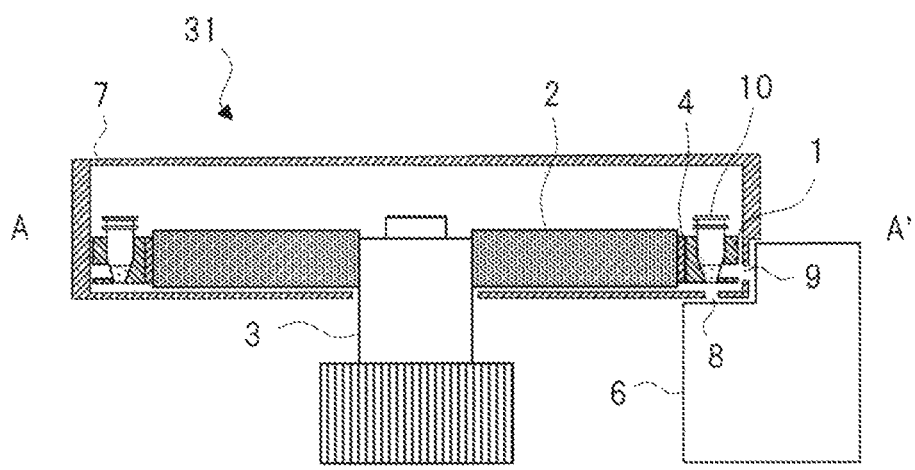
FIG. 2 is a sectional view illustrating a structure example between A-A' of FIG. 1.

FIG. 1 is a top view illustrating a structure example of a main part of a nucleic acid analysis device according to a first embodiment of the present invention. FIG. 2 is a sectional view illustrating a structure example between A-A' of FIG. 1. In a nucleic acid analysis device 31 illustrated in FIG. 1 and FIG. 2, a plurality of (in this embodiment, twelve) temperature adjusting blocks 1 is disposed along the outer periphery around the center axis of a carousel 2. The temperature adjusting blocks are driven to rotate around a rotation shaft 3. Between each of the plurality of temperature adjusting blocks 1 and the carousel 2 is provided a Peltier element 4. The temperature of the temperature adjusting block 1 is adjusted by controlling the Peltier element 4 while the temperature is monitored with a temperature sensor 5 mounted in the temperature adjusting block 1. A set of the Peltier element 4 and the temperature sensor 5 is provided for each of the temperature adjusting block 1, so that the temperature of each temperature adjusting block 1 is adjusted independently.

At the outer periphery of the carousel 2, a photometer 6 is disposed. Here, as one example, two photometers 6 are shown which use the light with the different wavelengths. Alternatively, one photometer 6 or three or more photometers 6 may be disposed at the outer periphery of the carousel 2. All the temperature adjusting blocks 1 move on the same circumference by the rotational driving; therefore, the relative position between the photometer 6 and the temperature adjusting block 1 when passing in front of the photometer 6 is the same for all the temperature adjusting blocks 1.

The plurality of temperature adjusting blocks 1 and the carousel 2 are together covered with a shielding plate 7 in order to reduce the optical disturbance when the analysis is conducted using the photometer 6. In the analysis, a tube (reaction container) 10 including a reaction solution (sample) in which the reagent and the like are mixed in the nucleic acid is held by the temperature adjusting block (holding member) 1. Each of the temperature adjusting blocks 1 is provided with an excitation light delivery window 8 for receiving the excitation light from the photometer 6, and a fluorescence detection window 9 for the photometer 6 to take in the fluorescence. Here, the excitation light delivery window 8 is disposed on a lower surface side of the temperature adjusting block 1 and the fluorescence detection window 9 is disposed on a side surface side of the temperature adjusting block 1; however, the windows can be set freely in accordance with the structure of the photometer.

<<Details of Photometer>>

Figure 3:
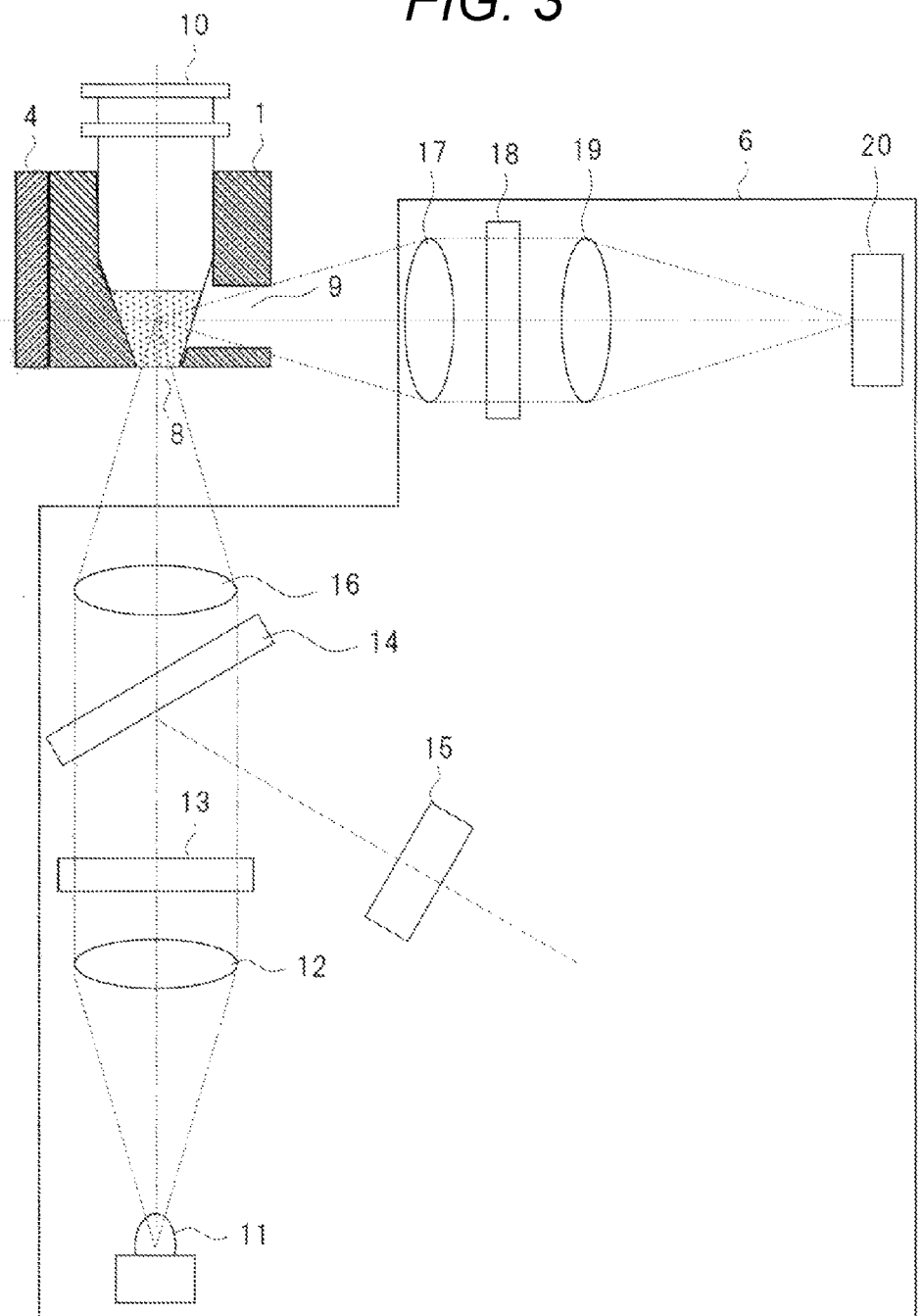
FIG. 3 is a schematic view illustrating a detailed structure example of a photometer in the nucleic acid analysis device in FIG. 1 and FIG. 2.

FIG. 3 is a schematic view illustrating a detailed structure example of the photometer in the nucleic acid analysis device in FIG. 1 and FIG. 2. In the photometer 6 illustrated in FIG. 3, the excitation light delivered from an LED (Light Emitting Diode) 11 as a light source becomes parallel light through a lens 12, and then goes through an excitation light filter (bandpass filter) 13 so that only the necessary wavelength component is extracted. Part of the light having passed through the excitation light filter 13 is reflected on a half-mirror 14, and enters an excitation light monitor detector (second detector) 15. The excitation light monitor detector 15 includes, for example, a photoelectric conversion diode (PD: Photodiode) or the like.

On the other hand, the remaining light having passed through the half-mirror 14 is condensed by a lens 16 and enters the excitation light delivery window 8 of the temperature adjusting block (holding member) 1. The temperature adjusting block 1 holds the tube (reaction container) 10 including the reaction solution (sample) in which the reagent and the like are mixed in the nucleic acid. Irradiating the temperature adjusting block 1 holding the tube 10 with the excitation light condensed by the lens 16 causes the reaction solution in the tube 10 to react with the excitation light and then emit the fluorescence. The fluorescence emitted from the fluorescence detection window 9 of the temperature adjusting block 1 becomes parallel light again through a lens 17 and goes through a fluorescence filter (bandpass filter) 18 so that only the necessary wavelength component is extracted. The light having passed through the fluorescence filter 18 is condensed by a lens 19 and enters a fluorescence detector (first detector) 20. The fluorescence detector 20 includes, for example, a photoelectric conversion diode (PD).

For example, the LED 11 as the light source always emits the excitation light and the excitation light monitor detector 15 and the fluorescence detector 20 always perform the detection. The excitation light monitor detector 15 and the fluorescence detector 20 generate detection signals (current or voltage) in accordance with the light intensity, and the detection signals are subjected to A/D conversion through a signal amplifying circuit and then transferred to a signal processing circuit. However, if all the detection signals are always processed, the nucleic acid analysis device 31 is burdened heavily; therefore, the nucleic acid analysis device 31 triggers just before the temperature adjusting block 1 passes in front of the photometer 6, and controls to stop to acquire the detection signal just after the block 1 passes. The analysis of the nucleic acid by such control typically provides the detection signals as illustrated in FIG. 4.

Figure 4:
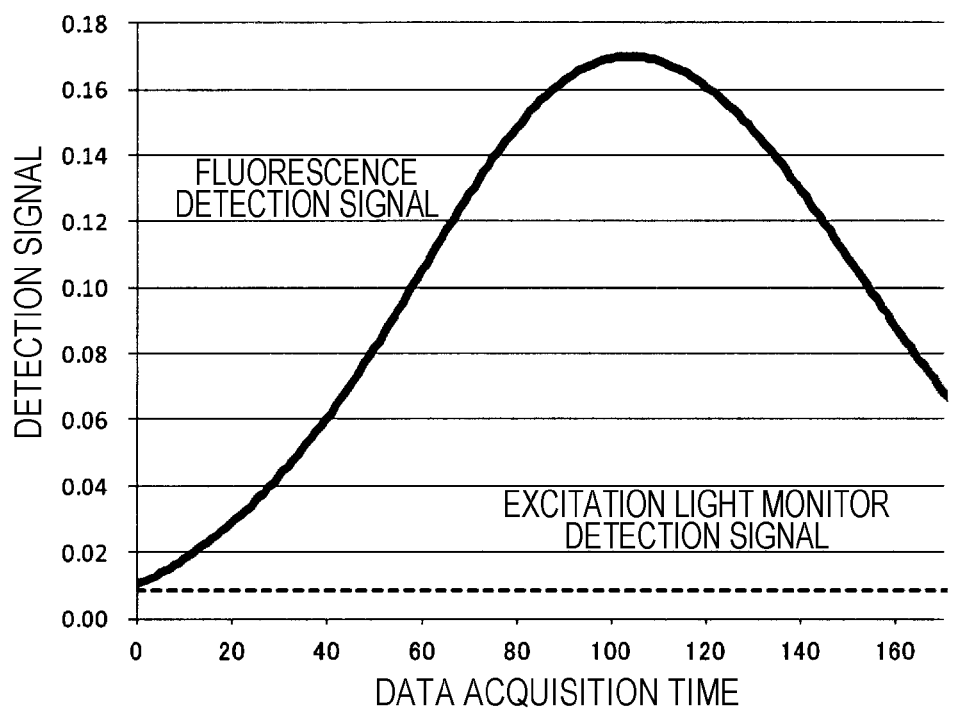
FIG. 4 illustrates an example of how the detection signals obtained in analyzing the nucleic acid by an excitation light monitor detector and a fluorescence detector in FIG. 3 shift over time.

FIG. 4 is a diagram illustrating an example of how the detection signals obtained in the analysis of the nucleic acid by the excitation light monitor detector and the fluorescence detector in FIG. 3 shift over time. The detection signals from the excitation light monitor detector 15 are at the substantially constant values. On the other hand, the detection signals from the fluorescence detector 20 are signals having a mountain-like waveform along the time, and the signal is the maximum at the time when the center line of the temperature adjusting block 1 to be measured passes the optical axis of the LED 11 of the photometer 6. The signals include electric noises; therefore, many nucleic acid analysis devices conduct the analysis of the nucleic acid by fitting a curve of the waveform of the detection signals in accordance with a certain rule for the approximate curve, acquiring the peak value of the approximate curve, and observing the change.

<<Details of Device Diagnosis Method>>

Next, description is made of a device diagnosis method for detecting the abnormality of the light source or the detector (trouble, performance deterioration) in the nucleic acid analysis device with the aforementioned structure.

Figure 5:
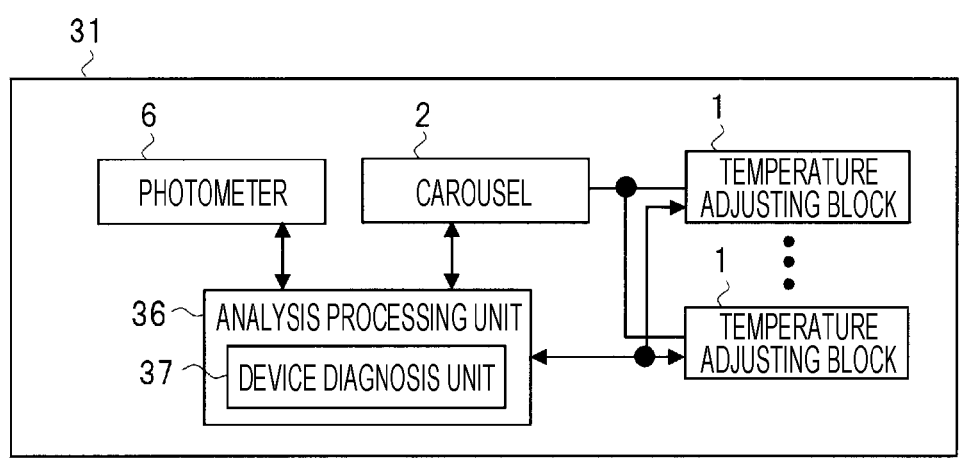
FIG. 5 is a block diagram schematically illustrating a main structure example of functions of the nucleic acid analysis device in FIG. 1 and FIG. 2.

FIG. 5 is a block diagram schematically illustrating a main structure example of the functions of the nucleic acid analysis device in FIG. 1 and FIG. 2. The nucleic acid analysis device 31 illustrated in FIG. 5 includes the plurality of temperature adjusting blocks 1, the carousel 2, and the photometer 6, and moreover an analysis processing unit 36 that controls these. The analysis processing unit 36 includes mainly a computer system, etc. Based on a predetermined process sequence, the analysis processing unit 36 adjusts the temperature of each temperature adjusting block 1, controls the rotation of the carousel 2, controls the photometer 6, and so on. The analysis processing unit 36 processes the signals obtained by each detector in the photometer 6. Here, the analysis processing unit 36 includes a device diagnosis unit 37.

Figure 6:
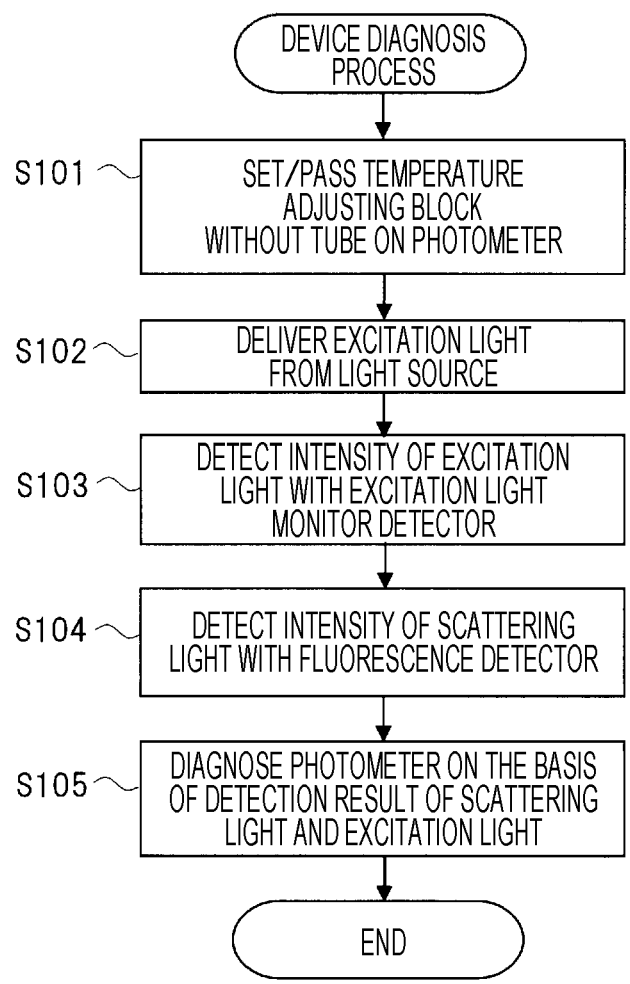
FIG. 6 is a flowchart illustrating an example of a process content of a device diagnosis unit in FIG. 5.

FIG. 6 is a flowchart illustrating an example of the process content of the device diagnosis unit in FIG. 5. For example, the device diagnosis unit 37 is activated just after the power is input to the nucleic acid analysis device 31 and executes the process in FIG. 6. First, the device diagnosis unit 37 sets the temperature adjusting block (holding member) 1, which does not hold the tube (reaction container) 10 illustrated in FIG. 3, on the photometer 6 or let the block 1 pass through the control of the carousel 2 (Step S101). Next, the device diagnosis unit 37 causes the LED (light source) 11 in the photometer 6 to deliver the excitation light toward the temperature adjusting block 1 (Step S102). In general, since the light source is instable just after the light is turned on, the light may be delivered in advance. If the temperature adjusting block 1 passes, the LED (light source) 11 may be turned on in advance.

Next, the device diagnosis unit 37 has the excitation light monitor detector (second detector) 15 detect the intensity of the excitation light delivered in Step S102 (Step S103). Subsequently, the device diagnosis unit 37 has the fluorescence detector (first detector) 20 detect the intensity of the scattering light generated in Step S102 (Step S104). Here, the scattering light can be generated not just in the temperature adjusting block 1 made of aluminum or the like but also in any other places. For example, since the temperature adjusting block 1 and the carousel 2 are covered with the shielding plate 7 as illustrated in FIG. 2, the scattering light is generated in various places in the space covered with the shielding plate 7. The scattering light enters the fluorescence detector 20 through the fluorescence detection window 9.

Subsequently, on the basis of the intensity of the excitation light detected in Step S103 and the intensity of the scattering light detected in Step S104, the device diagnosis unit 37 diagnoses the presence or absence of the abnormality (trouble or performance deterioration) of the photometer 6 (Step S105). Detailed description will be made of the method of diagnosing the presence or absence of the abnormality of the photometer 6 in Step S105.

Figure 7:
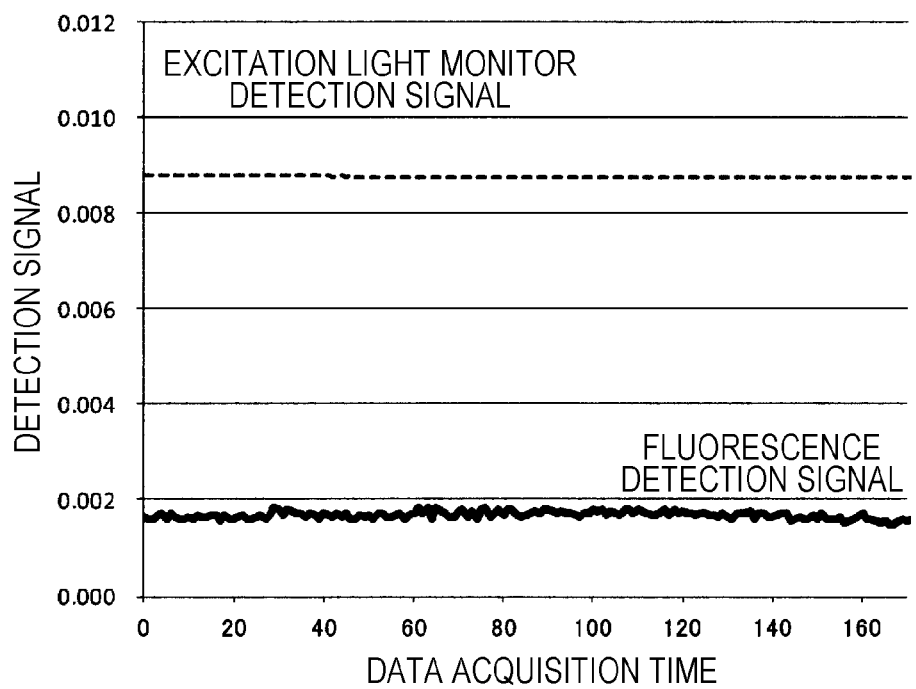
FIG. 7 illustrates an example of how the detection signals obtained by the excitation light monitor detector and the fluorescence detector shift over time in the device diagnosis flow in FIG. 6.

FIG. 7 is a diagram illustrating an example of how the detection signals obtained by the excitation light monitor detector and the fluorescence detector shift over time in the device diagnosis flow in FIG. 6. The detection signals from the excitation light monitor detector 15 are at the substantially constant values. On the other hand, the detection signals from the fluorescence detector 20 are very weak but are observed. This is because part of the excitation light having entered the temperature adjusting block 1 is scattered and enters the fluorescence detector 20. In the example of FIG. 7, the condition under which the device is actually used is considered and the diagnosis is conducted in the state that the light emission power of the LED 11 is set to the same level as that in the case of FIG. 4. In some cases, alternatively, the light emission power of the LED 11 can be increased so that the diagnosis is conducted with the increased scattering light.

Figure 8:
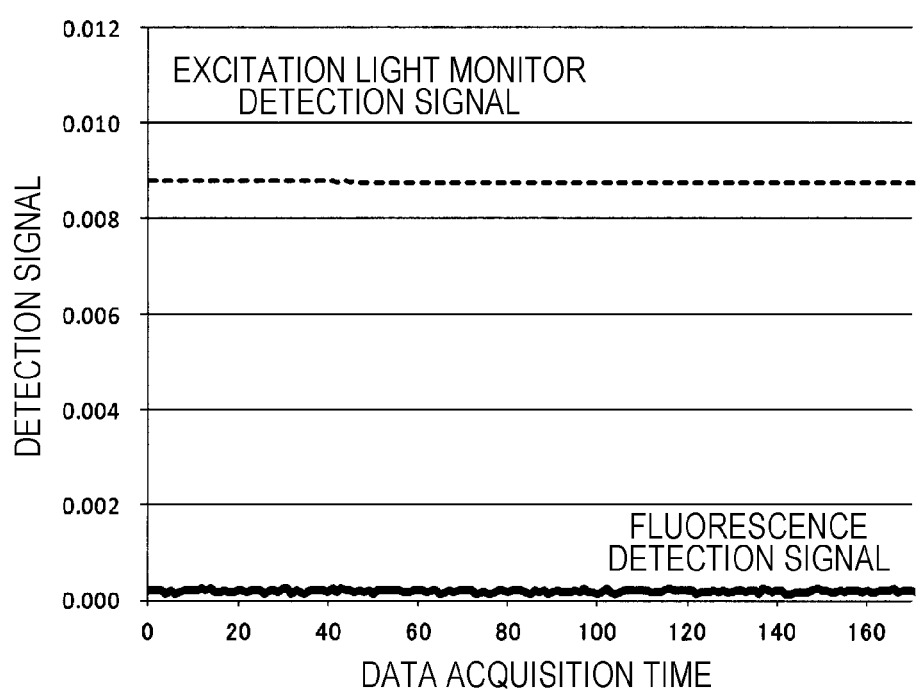
FIG. 8 illustrates an example of how the detection signals obtained by the excitation light monitor detector and the fluorescence detector shift over time in the occurrence of a trouble in the fluorescence detector in the device diagnosis flow in FIG. 6.

FIG. 8 is a diagram illustrating an example of how the detection signals obtained by the excitation light monitor detector and the fluorescence detector shift over time in the occurrence of the trouble in the fluorescence detector in the device diagnosis flow in FIG. 6. In a manner similar to the case of FIG. 7, the detection signals from the excitation light monitor detector 15 are at the substantially constant values. On the other hand, the detection signals from the fluorescence detector 20 are weaker than those in the case of FIG. 7. These weak signals are due to the electric noise or the optical disturbance from the outside.

Therefore, a threshold is set in advance between the level of the fluorescence detection signal in FIG. 7 and the level of the fluorescence detection signal in FIG. 8; if the value is lower than the threshold, an alarm may be issued. This enables the detection of the abnormality of the fluorescence detector 20. Similarly, a threshold may be set in advance for the detection signal from the excitation light monitor detector 15. If the value is lower than the threshold, an alarm may be issued. This enables the detection of the abnormality of the excitation light monitor detector 15.

Figure 9A:
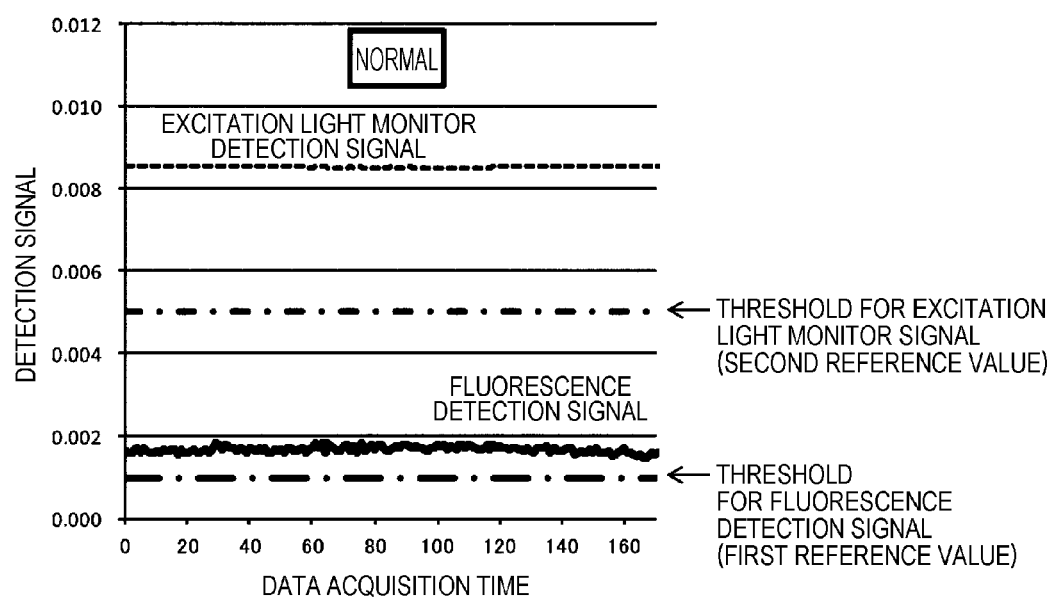
FIG. 9A is a diagram summarizing an example of the relation between the combination of the detection signals from the excitation light monitor detector and the fluorescence detector, and the abnormality of the component determined therefrom in the device diagnosis flow in FIG. 6.

FIG. 9A to FIG. 9D are diagrams summarizing an example of the relation between the combination of the detection signals from the excitation light monitor detector and the fluorescence detector, and the abnormality of the component determined therefrom in the device diagnosis flow in FIG. 6. FIG. 9A schematically illustrates FIG. 7. The intensity of the excitation light represented by the level of the excitation light monitor detection signal is higher than the reference intensity (second reference value) represented by the excitation monitor signal threshold that has been set in advance, and the intensity of the scattering light represented by the fluorescence detection signal is higher than the reference intensity (first reference value) represented by the fluorescence detection signal threshold that has been set in advance. In this case, the device diagnosis unit 37 determines that the LED 11, the excitation light monitor detector 15, and the fluorescence detector 20 are normal.

Figure 9B:
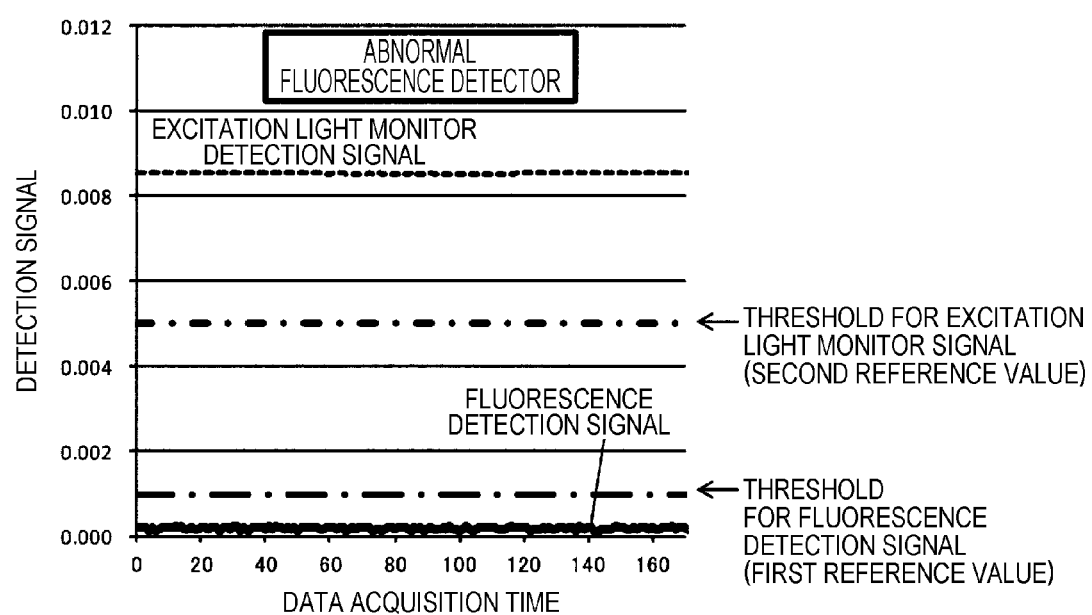
FIG. 9B is a diagram subsequent to FIG. 9A.

FIG. 9B schematically illustrates FIG. 8. The intensity of the excitation light is higher than the reference intensity (second reference value), and the intensity of the scattering light is lower than the reference intensity (first reference value). In this case, the detection signals from the excitation light monitor detector 15 are normally obtained; therefore, the device diagnosis unit 37 determines that the LED 11 and the excitation light monitor detector 15 do not have the abnormality. On the other hand, the intensity of the scattering light is lower than the reference intensity (first reference value) though the excitation light is normally output; therefore, the device diagnosis unit 37 determines that the fluorescence detector 20 has the abnormality.

Figure 9C:
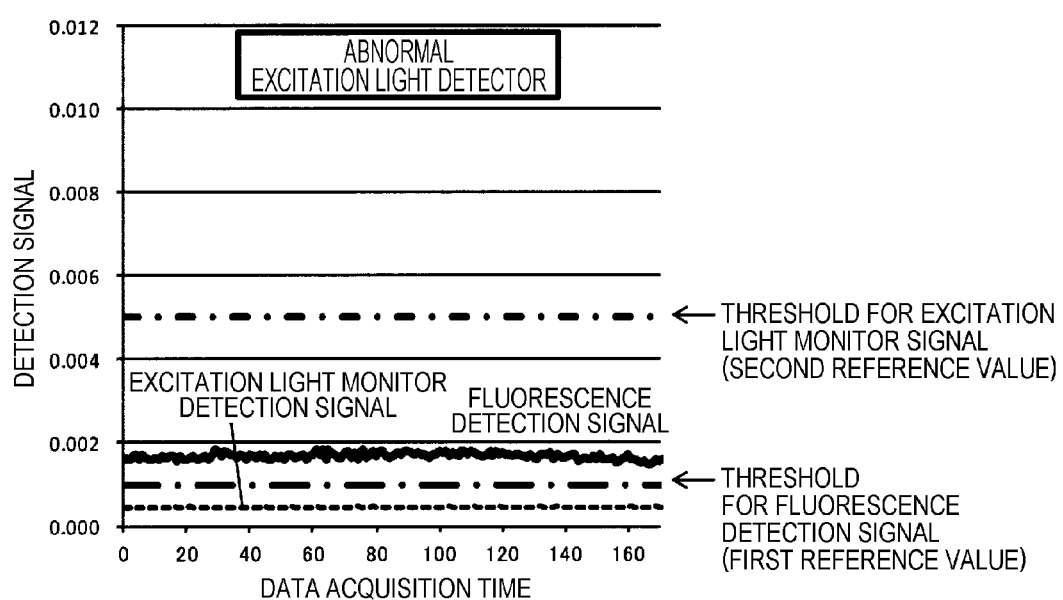
FIG. 9C is a diagram subsequent to FIG. 9B.

In FIG. 9C, the intensity of the scattering light is higher than the reference intensity (first reference value), but the intensity of the excitation light is lower than the reference intensity (second reference value). That the intensity of the scattering light is higher than the reference intensity (first reference value) means the operation of the fluorescence detector 20 is normal and the scattering light normally enters the fluorescence detector 20. This indicates that the LED 11 is normal. In this case, the device diagnosis unit 37 therefore determines the excitation light monitor detector 15 has the abnormality.

Figure 9D:
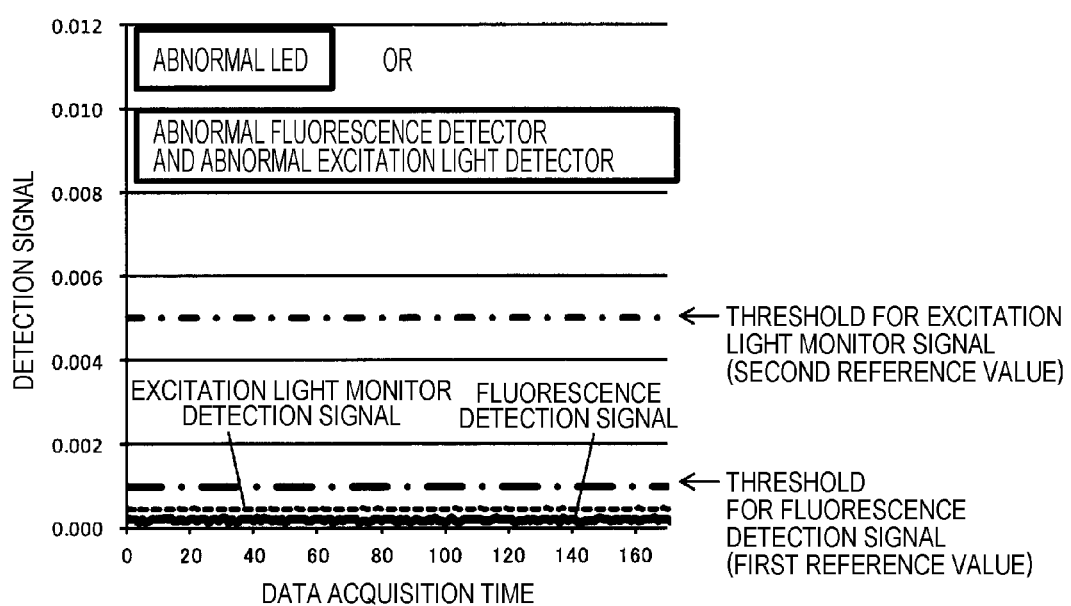
FIG. 9D is a diagram subsequent to FIG. 9C.

In FIG. 9D, the intensity of the excitation light is lower than the reference intensity (second reference value), and the intensity of the scattering light is also lower than the reference intensity (first reference value). In this case, the following two patterns are assumed: (1) the LED 11 is abnormal (whether the excitation light monitor detector 15 and the fluorescence detector 20 are normal or abnormal is not known); and (2) the LED 11 is normal and neither the excitation light monitor detector 15 nor the fluorescence detector 20 is normal. Generally speaking, it is very unlikely that the two elements are both in trouble at the same time; therefore, in this case, the device diagnosis unit 37 determines the LED 11 is abnormal.

The first reference value and the second reference value are not necessarily constant values, and may be changed as necessary.

<<Main Effect of First Embodiment>>

By the use of the nucleic acid analysis device according to the first embodiment, the abnormality of the device, etc. can be detected quickly and which component has caused the abnormality (light source or detector) can be specified. That is to say, without the process of attaching and detaching the component as disclosed in PTL 1, the device can be diagnosed just by delivering the excitation light to the temperature adjusting block 1 not holding the tube 10, and detecting the scattering light. Thus, the diagnosis can be conducted in a short period of time. In addition, along with the delivery of the excitation light, the excitation light and the scattering light are detected together. This can specify the component that has caused the abnormality in the device, which is different from PTL 1 to PTL 3. In the device diagnosis, the advanced monitoring function as disclosed in PTL 3 is not particularly required and the component which is usually mounted in the nucleic acid analysis device can be used to diagnose the device. This is advantageous in terms of cost.

Another comparative example is a method of diagnosing the device using a tube including a standard sample or the like for detecting the abnormality in a period of diagnosing the device just after the power input. In the nucleic acid analysis device, however, it is not always easy to prepare the standard sample and even if the standard sample should be prepared, the process of loading and unloading the tube is required. On the other hand, the method according to this embodiment does not need the process of loading and unloading the tube and the diagnosis period can be shortened and the cost required to prepare the standard sample can be reduced. In addition, in some nucleic acid analysis devices, the usual sample that has been unloaded is discarded automatically from the viewpoint of the safety of the device. However, the standard sample is desirably collected separately. That is to say, in the case of using the standard sample, the mechanism for collecting the standard sample is additionally necessary. In the method of this embodiment, however, such a mechanism is not necessary.

Second Embodiment

<<Details of Device Diagnosis Method (Application Example)>>

In the aforementioned first embodiment, the device is diagnosed by detecting the excitation light and the scattering light for one temperature adjusting block 1 not holding the tube 10. In fact, however, the intensity of the scattering light in the state that the tube 10 is not held by the temperature adjusting block 1 (i.e., detection signal of the fluorescence detector 20) is weak, and the scattering light might increase or decrease depending on the small shape difference of each component. Therefore, determining the important fact, i.e., the abnormality of the component, based on the result of diagnosing one temperature adjusting block 1 may increase the risk of the wrong diagnosis.

Figure 10:
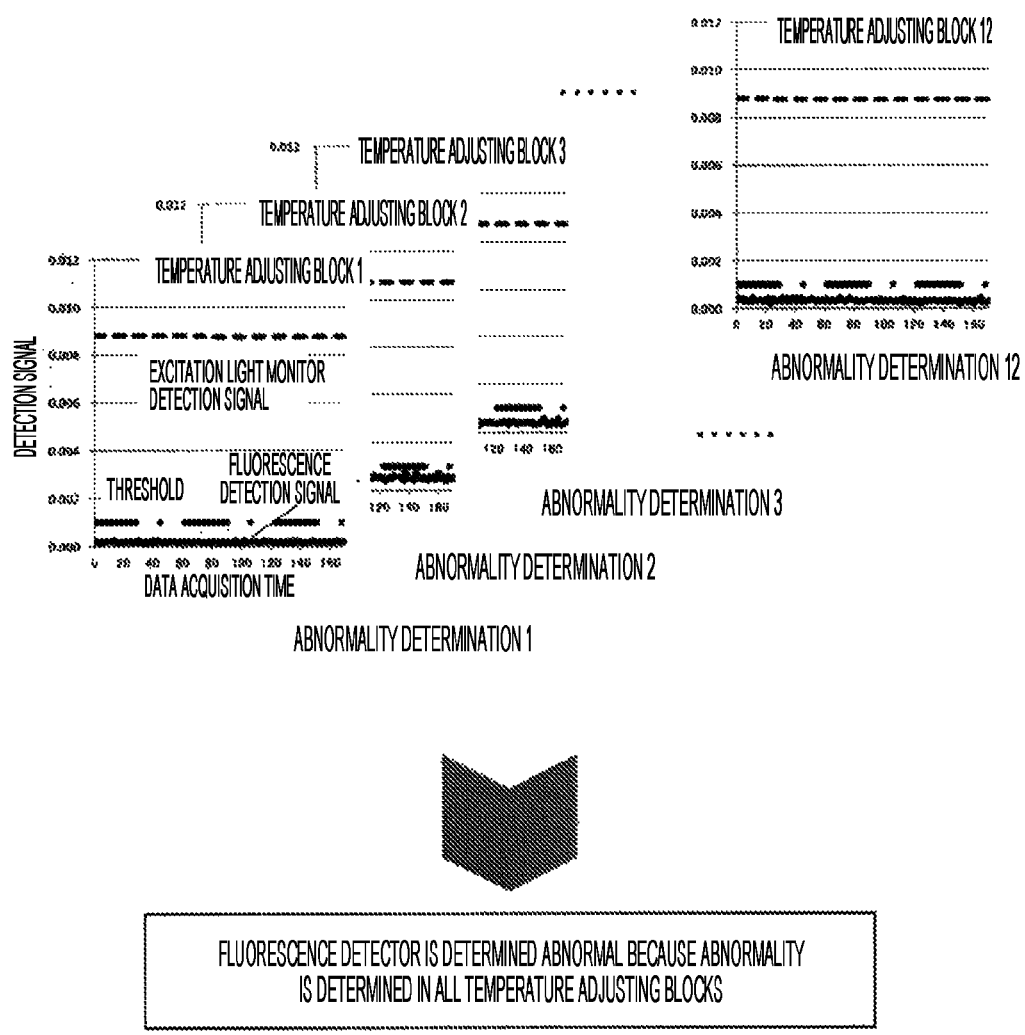
FIG. 10 is an explanatory view schematically illustrating an example of a diagnosis method for a nucleic acid analysis device according to a second embodiment of the present invention.

In view of the above, for example, it is efficient to use the method as illustrated in FIG. 10. FIG. 10 is an explanatory view schematically illustrating an example of the diagnosis method for the nucleic acid analysis device according to a second embodiment of the present invention. In FIG. 10, the plurality of (here, twelve) temperature adjusting blocks 1 illustrated in FIG. 1 is used and for each of the twelve temperature adjusting blocks 1, the excitation light and the scattering light are detected by the photometer 6. Thus, the device is diagnosed.

Specifically, the device diagnosis unit 37 in FIG. 5 executes the process from Step S102 to Step S104 in FIG. 6 for each temperature adjusting block 1 while the carousel 2 is controlled to rotate so that the twelve temperature adjusting blocks 1 sequentially pass the photometer 6. However, the detection signals of the excitation light monitor detector 15 in Step S103 are considered substantially the same between the temperature adjusting blocks 1; therefore, the process in Step S103 may be performed for less than 12 (for example, one) temperature adjusting blocks 1 only.

The device diagnosis unit 37 compares the twelve detection signals from the fluorescence detector 20 and the twelve or less detection signals from the excitation light monitor detector 15 obtained in Steps S102 to S104 with the diagnosis criterion which has been set in advance, and based on this, the device diagnosis unit 37 diagnoses the device in Step S105 in FIG. 6. In FIG. 10, as one example of the diagnosis criterion, the device diagnosis unit 37 determines that the fluorescence detector 20 has the abnormality if the intensity of the excitation light by the excitation light monitor detector 15 is higher than the reference intensity (second reference value) and the intensity of each scattering light in accordance with each of the twelve detection signals from the fluorescence detector 20 is lower than the reference intensity (first reference value).

Thus, the reliability of the device diagnosis can be improved. Note that the diagnosis criterion is not limited to that described above, and for example, the abnormality may be determined based on the average value of the twelve detection signals, or the determination may be made based on the proportion of the signals whose intensity is lower than the reference intensity (first reference value) among the twelve detection signals. Moreover, the twelve detection signals from the fluorescence detector 20 are not necessarily used entirely. Some of them may be omitted to make the determination.

<<Main Effect of Second Embodiment>>

By the use of the nucleic acid analysis device according to the second embodiment, the reliability of making the important determination on the abnormality of the component can be increased and the risk of the wrong diagnosis can be reduced.

Third Embodiment

<<Details of Device Diagnosis Method (Modified Example)>>

The device diagnosis method described in the first embodiment and the second embodiment can be carried out in the state that the tube 10 is not inserted in the temperature adjusting block 1. Therefore, for example, the method can be carried out easily in a short time in a preparation period while the analysis is awaited after the power is input to the nucleic acid analysis device. On the other hand, the abnormality of the photometer 6 (i.e., the light source or the detector) can occur during the analysis of the nucleic acid after the preparation period (i.e., during the normal operation). In the occurrence of the abnormality in the analysis, the possibility that the analysis result might be wrong needs to be exhibited, and it is still necessary to detect the abnormality of the device.

Figure 11:
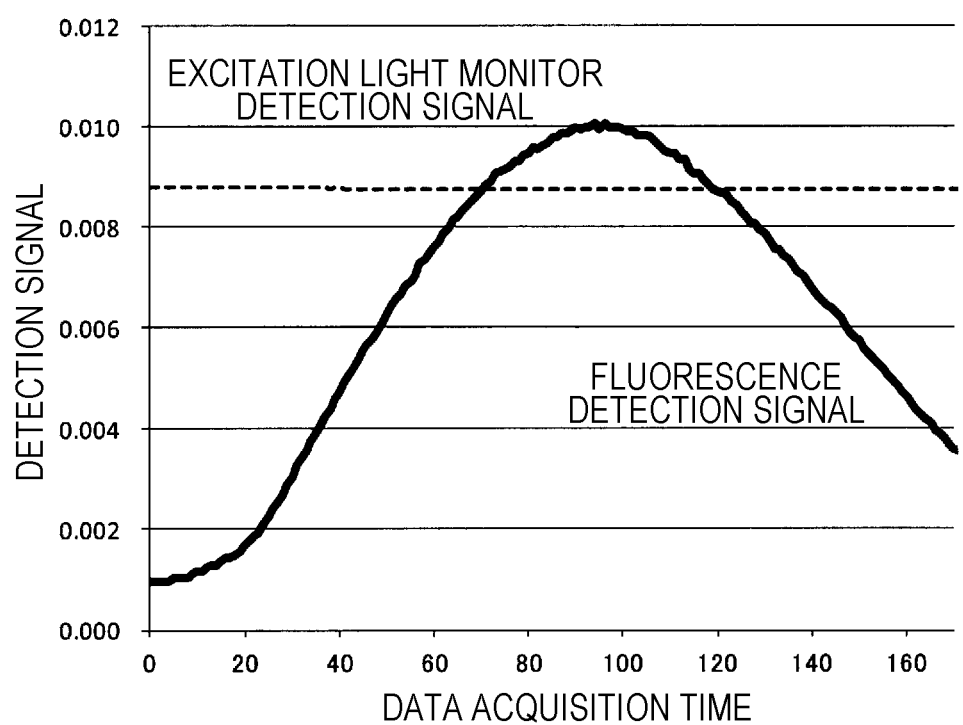
FIG. 11 is a diagram illustrating an example of how the detection signals obtained by the excitation light monitor detector and the fluorescence detector shift over time in a nucleic acid analysis device according to a third embodiment of the present invention.

FIG. 11 is a diagram illustrating an example of how the detection signals obtained by the excitation light monitor detector and the fluorescence detector shift over time in the nucleic acid analysis device according to a third embodiment of the present invention. FIG. 11 shows the waveform of each detection signal when the hollow tube 10 is held by the temperature adjusting block 1. The detection signals from the excitation light monitor detector 15 are at the substantially constant values. On the other hand, the detection signals from the fluorescence detector 20 have the mountain-like waveform along the time. This is because the scattering light is increased due to the existence of the tube 10. In general, when the reagent or the like is included in the tube 10, the signal level is further increased due to the influence therefrom.

In view of this, after the analysis is started, the threshold of the detection signal from the fluorescence detector 20 is set to be higher than the initial threshold (i.e., in the state that the tube 10 is not in the temperature adjusting block 1). This enables to detect the abnormality of the fluorescence detector 20 earlier even if the analysis is already started (i.e., in the normal operation). If the degree of the abnormality of the fluorescence detector 20 is large, the fluorescence detection signals are at the level similar to that of FIG. 8 even though the tube is in the temperature adjusting block 1. Therefore, in some cases, the threshold does not need to be set separately. However, for determining the tendency of the abnormality of the fluorescence detector 20 earlier, the threshold is desirably set separately. In regard to the detection signals from the excitation light monitor detector 15, the signals do not change either before the start of the analysis or during the analysis. Therefore, the device diagnosis can be carried out in the analysis without setting the threshold separately.

In regard to the fluorescence detector 20 after the start of the analysis, it is desired that the diagnosis based on the waveform of one detection signal is avoided, which is similar to the case of the second embodiment. Therefore, in the manner similar to the second embodiment, it is desired that a plurality of detection signals from the fluorescence detector 20 is acquired while the plurality of temperature adjusting blocks 1 is let pass relative to the photometer 6 sequentially and the abnormality of the fluorescence detector 20 is determined based on a predetermined diagnosis criterion in the third embodiment.

The first and second embodiments have described the method in which the device diagnosis is carried out in the preparation period where the analysis is awaited after the power is input to the nucleic acid analysis device, and the third embodiment has described the method in which the device diagnosis is carried out during the analysis. Alternatively, in a manner similar to the first and second embodiments, the device diagnosis may be carried out after the analysis is over and in the preparation period where the next analysis is awaited. Further alternatively, the device diagnosis may be carried out after the analysis is over and before the power is turned off.

Fourth Embodiment

<<Structure of Nucleic Acid Analysis Device>>

Figure 12:
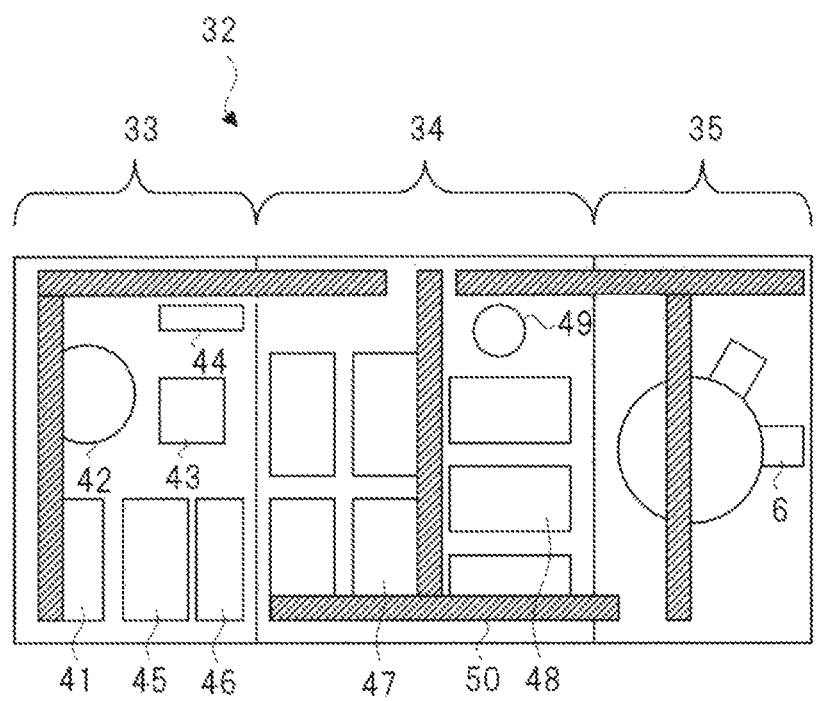
FIG. 12 is a top view illustrating a schematic structure example of a nucleic acid analysis device according to a fourth embodiment of the present invention.

FIG. 12 is a top view illustrating a schematic structure example of a nucleic acid analysis device according to a fourth embodiment of the present invention. In FIG. 12, a nucleic acid analysis device 32 includes: a nucleic acid extracting unit 33 that extracts the nucleic acid from a specimen, a reagent mixing unit 34 that dispenses a reagent to the extracted nucleic acid and mixes the reagent and the nucleic acid; and a nucleic acid analyzing unit 35 that detects the fluorescence by adjusting the temperature of the mixed reaction solution.

The nucleic acid extracting unit 33 includes a specimen loading unit 41, a centrifuge unit 42, a retracting chamber 43, a tube loading unit 44, an extracted reagent storage 45, a consumption article storage 46, and the like. The nucleic acid extracting unit 33 has a function of removing the unnecessary component from the specimen and extracting only the nucleic acid necessary for the analysis, though the detailed description is omitted here. The reagent mixing unit 34 includes an analysis reagent storage 47, a consumption article storage 48, a mixing unit 49, and the like, though the detailed description is omitted here. The reagent mixing unit 34 has a function of mixing a reagent for analysis to the nucleic acid extracted by the nucleic acid extracting unit 33. The structure of the nucleic acid analyzing unit 35 is the same as the nucleic acid analysis device 31 illustrated in FIG. 1, and has a function of analyzing the nucleic acid in the final step. The transportation of the tube between the units is carried out by a robot arm 50.

The analysis executer activates the nucleic acid analysis device 32, and sets the specimen, the reagent, the tube, and other consumption articles and then starts the analysis. On this occasion, with the use of the nucleic acid analysis device 32 having the nucleic acid extracting unit 33 and the reagent mixing unit 34 as illustrated in FIG. 12, the abnormality (trouble, performance deterioration) of the photometer 6 including the light source and the detector can be detected early at the stage where the device is activated (i.e., at the preparation stage of the device just after the power is input). If the photometer 6 is normal, the nucleic acid analysis device 32 shifts to the normal operation and starts the pre-treatment for the analysis with the nucleic acid extracting unit 33 and the reagent mixing unit 34.

As a result, if the abnormality has been found in the photometer 6, the photometer 6 can be repaired before the pre-treatment for the analysis is performed on the specimen (specifically, before the reagent is mixed and more desirably before the nucleic acid is extracted). Thus, the specimen is not wasted. As a comparative example, the nucleic acid extracting unit 33, the reagent mixing unit 34, and the nucleic acid analyzing unit 35 are formed by the separate devices. In this case, such a situation may occur that the reagent mixing is already performed. In the nucleic acid analysis device 32 in this embodiment, the device diagnosis can be carried out in a short period of time just after the power is input to the device as described in the first embodiment. Therefore, if the diagnosis result is normal, the throughput of the device can be increased.

The invention made by the present inventor has been specifically described based on the embodiments; however, the present invention is not limited to the embodiments above and various changes are possible without departing the content thereof. For example, the embodiments above are described to help the understanding of the present invention and do not limit the invention to the one having all the described structures. A part of the structure of one embodiment can be replaced by the structure of another embodiment and the structure of one embodiment can be added to the structure of another embodiment. Moreover, a part of the structure of each embodiment can be added to, deleted from, or replaced by another structure.

For example, the description has been made of the nucleic acid analysis device for which the use of the device diagnosis method according to the embodiment is particularly effective. However, the device is not necessarily limited to the nucleic acid analysis device and the present invention can be similarly applied to any device in which the reaction container is set to the holding member and the sample in the reaction container is analyzed using the photometer and in this case, the similar effect may be obtained.

REFERENCE SIGNS LIST 1 temperature adjusting block
2 carousel
3 rotation shaft
4 Peltier element
5 temperature sensor
6 photometer
7 shielding plate
8 excitation light delivery window
9 fluorescence detection window
10 tube
11 LED
12, 16, 17, 19 lens
13 excitation light filter
14 half-mirror
15 excitation light monitor detector (second detector)
18 fluorescence filter
20 fluorescence detector (first detector)
31, 32 nucleic acid analysis device
33 nucleic acid extracting unit
34 reagent mixing unit
35 nucleic acid analyzing unit
36 analysis processing unit
37 device diagnosis unit
41 specimen loading unit
42 centrifuge unit
43 retracting chamber
44 tube loading unit
45 extracted reagent storage
46, 48 consumption article storage
47 analysis reagent storage
49 mixing unit
50 robot arm

The invention claimed is:

1. An analysis device comprising:
two or more light source/detector pairs including a light source that delivers light and a detector that detects light; and
a device diagnosis unit that detects a state of the light source and the detector included in the two or more light source/detector pairs on the basis of a result of detecting the light delivered from the light source included in the two or more light source/detector pairs by the detector constituting a pair with the light source, wherein the device diagnosis unit is configured to detect the state of the light source and the detector included in the two or more light source/detector pairs on the basis of comparison between a detection result of the detector and a predetermined reference value,
the analysis device further comprising a holding member that holds an analysis target, wherein any detector among the detectors in the two or more light source/detector pairs detects part of light delivered to the holding member,
wherein the light source and the detector included in the two or more light source/detector pairs include a first light source, a first detector, and a second detector,
wherein the first detector detects part of light delivered from the first light source to the holding member, and
wherein the second detector detects intensity of the light delivered from the first light source,
wherein the device diagnosis unit determines that the first detector is abnormal when the intensity of the light detected by the first detector is lower than a predetermined first reference value and the intensity of the light detected by the second detector is higher than a predetermined second reference value, and that the second detector is abnormal when the intensity of the light detected by the first detector is higher than the predetermined first reference value and the intensity of the light detected by the second detector is lower than the predetermined second reference value.

2. The analysis device according to claim 1, wherein the holding member is one of a plurality of holding members,
wherein the first detector detects part of light delivered to the plurality of holding members,
wherein the holding member is one of a plurality of holding members,
wherein the analysis device is a nucleic acid analysis device that analyzes nucleic acid, and
wherein each of the plurality of holding members has a mechanism capable of adjusting temperature independently.

3. The analysis device according to claim 2, further comprising:
a reagent mixing unit that mixes a reagent in nucleic acid in a reaction container to prepare a sample; and
an analyzing unit that analyzes the sample,
wherein the device diagnosis unit is configured to be activated just after power is input to the nucleic acid analysis device, and
wherein the device diagnosis unit is configured to start a process of the reagent mixing unit when a state of the light source and the detector included in the two or more light source/detector pairs is normal on the basis of comparison between detection results of the first detector and the second detector and a predetermined reference value.

4. An analysis device comprising:
two or more light source/detector pairs including a light source that delivers light and a detector that detects light; and
a device diagnosis unit that detects a state of the light source and the detector included in the two or more light source/detector pairs on the basis of a result of detecting the light delivered from the light source included in the two or more light source/detector pairs by the detector constituting a pair with the light source, wherein the device diagnosis unit is configured to detect the state of the light source and the detector included in the two or more light source/detector pairs on the basis of comparison between a detection result of the detector and a predetermined reference value,
the analysis device further comprising a holding member that holds an analysis target, wherein any detector among the detectors in the two or more light source/detector pairs detects part of light delivered to the holding member,
wherein the light source and the detector included in the two or more light source/detector pairs include a first light source, a first detector, and a second detector,
wherein the first detector detects part of light delivered from the first light source to the holding member, and
wherein the second detector detects intensity of the light delivered from the first light source, wherein the device diagnosis unit determines that the first light source is abnormal when the intensity of the light detected by the first detector is lower than a predetermined first reference value and the intensity of the light detected by the second detector is lower than a predetermined second reference value.

5. The analysis device according to claim 4,
wherein the holding member is one of a plurality of holding members,
wherein the analysis device is a nucleic acid analysis device that analyzes nucleic acid, and
wherein each of the plurality of holding members has a mechanism capable of adjusting temperature independently.

6. The analysis device according to claim 5, further comprising:
a reagent mixing unit that mixes a reagent in nucleic acid in a reaction container to prepare a sample; and
an analyzing unit that analyzes the sample,
wherein the device diagnosis unit is configured to be activated just after power is input to the nucleic acid analysis device, and
wherein the device diagnosis unit is configured to start a process of the reagent mixing unit when a state of the light source and the detector included in the two or more light source/detector pairs is normal on the basis of comparison between detection results of the first detector and the second detector and a predetermined reference value.

7. A diagnosis method for an analysis device including a holding member that holds a reaction container containing a sample, and a photometer including a light source that delivers light toward the holding member, a first detector that receives light emitted from the holding member in accordance with the delivery of the light from the light source, and a second detector that detects intensity of the light delivered from the light source, the method comprising:

a first step of causing the light source to deliver the light toward the holding member in a state of not holding the reaction container;
a second step of causing the first detector to detect light emitted from the holding member and causing the second detector to detect the intensity of the light delivered from the light source; and
a third step of causing the analysis device to diagnose the photometer on the basis of the intensity of the light detected by the first detector,
wherein in the third step, the analysis device determines that the first detector is abnormal when the intensity of the light detected by the first detector is lower than a predetermined first reference value and the intensity of the light detected by the second detector is higher than a predetermined second reference value, and that the second detector is abnormal when the intensity of the light detected by the first detector is higher than the first reference value and the intensity of the light detected by the second detector is lower than the second reference value.

8. The diagnosis method for the analysis device according to claim 7, wherein the analysis device determines that the light source is abnormal when the intensity of the light detected by the first detector is lower than the first reference value and the intensity of the light detected by the second detector is lower than the second reference value in the third step.

9. The diagnosis method for the analysis device according to claim 7,
wherein the holding member is one of a plurality of holding members,
wherein the first and second steps are carried out for each of the plurality of holding members, and
wherein the analysis device diagnoses the photometer by comparing detection results of the first and second detectors for each of the plurality of holding members with a predetermined diagnosis criterion in the third step.

* * * * *